United States Patent [19]

Turner

US005180417A

[11] Patent Number: 5,180,417
[45] Date of Patent: Jan. 19, 1993

[54] 4-((ARYLOXY)PHENOXY)FLUOROALK-ANOIC ACID DERIVATIVES AND THEIR HERBICIDAL USES

[75] Inventor: James A. Turner, Pleasant Hill, Calif.

[73] Assignee: DowElanco, Indianapolis, Ind.

[21] Appl. No.: 684,703

[22] Filed: Apr. 12, 1991

Related U.S. Application Data

[62] Division of Ser. No. 377,697, Jul. 10, 1989, Pat. No. 5,032,168.

[51] Int. Cl.$^5$ .................. C01D 471/02; A01N 43/00
[52] U.S. Cl. .................... 504/246; 546/114; 546/116; 548/169; 548/221; 504/267; 504/270
[58] Field of Search ............... 546/114, 116; 548/169, 548/221; 71/88, 90, 92

[56] References Cited

U.S. PATENT DOCUMENTS

| | | | |
|---|---|---|---|
| 4,731,108 | 3/1988 | Turner et al. | 71/94 |
| 4,900,354 | 2/1990 | Turner et al. | 71/94 |
| 4,976,772 | 12/1990 | Turner et al. | 71/92 |

Primary Examiner—C. Warren Ivy
Assistant Examiner—Raymond Covington
Attorney, Agent, or Firm—S. Preston Jones; Kenneth L. Loertscher

[57] ABSTRACT

Disclosed herein are derivatives of 4-((aryloxy)phenoxy)fluoroalkanoic acid and their use as active herbicides for the pre- and postemergent control of grassy weeds, especially in the presence of broadleaf crops.

12 Claims, No Drawings

4-((ARYLOXY)PHENOXY)FLUOROALKANOIC ACID DERIVATIVES AND THEIR HERBICIDAL USES

This is a divisional of application Ser. No. 377,697, filed Jul. 19, 1989, now U.S. Pat. No. 5,032,168.

BACKGROUND OF THE INVENTION

Compounds of the class constituting aryloxyphenoxyalkanoic acids and related compounds have been described as herbicides in the patent literature. These compounds have been prepared by making derivatives of the acid function thereof and bearing various groups or substituents on, primary, the aryl structure.

FIELD OF THE INVENTION

The present invention relates to novel highly active herbicidal compounds, compositions containing said compound and methods for the postermergent use thereof in the kill and control of grassy weeds. The invention relates especially to novel 4-((aryloxy)phenoxy)alkanoic acid derivatives, compositions containing said compounds and the postemergent herbicidal use thereof. In addition, the invention is also directed to the use of some of the novel herbicidal derivatives in the preparation of other novel herbicidal derivatives.

SUMMARY OF THE INVENTION

It has now been discovered that derivatives of aryloxyphenoxyalkanoic acids, particularly the propanoic acids, are highly active herbicidal compounds effective in the postemergent, systemic kill and control of grassy weeds.

The active aryloxyphenoxyalkanoic acid compounds of the present invention correspond to the formula

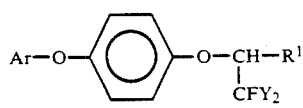

(I)

wherein
Ar represents

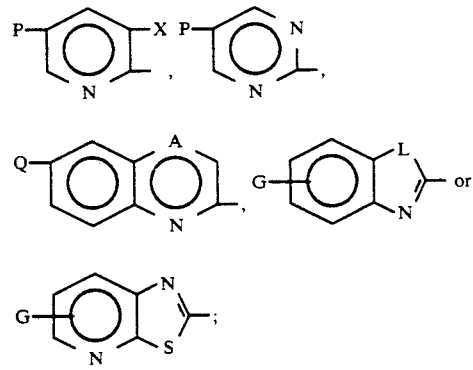

X represents —H, —Br, —Cl or —F;
each Y independently represents —H or —F;
A represents ≡N or ≡CH;
G represents, in the 5 or 6 ring position, —Br, —Cl, —F or —CF$_3$;
P represents —Br, —Cl, —I or —CF$_3$;
Q represents —Br, —Cl, —F, —I, —CH$_3$ or —CF$_3$;
R$^1$ represents —CH$_2$OH, —CN, —COOH, —COOM, —COOR$^2$,

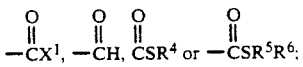

X$^1$ represents —Br or —Cl;
L represents oxygen or sulfur;
M represents an agriculturally acceptable cation;
R$^2$ represents C$_1$–C$_{12}$ alkyl, C$_3$–C$_{12}$ alkenyl, C$_3$–C$_{12}$ alkynyl, C$_3$–C$_{12}$ cycloalkyl, C$_1$–C$_{12}$ alkyl substituted with 1 or 2 bromo, chloro, fluoro or C$_1$–C$_4$ alkoxy substituents or R$^2$ represents phenyl substituted with 1 or 2 bromo, chloro, fluoro, C$_1$–C$_4$ alkyl, C$_1$–C$_4$ alkoxy or nitro substituents or R$^2$ represents the radical —N=C(R$^3$)$_2$ wherein each R$^3$ independently represents a C$_1$–C$_4$ alkyl;
R$^4$ represents C$_1$–C$_{12}$ alkyl, C$_3$–C$_{12}$ alkenyl, C$_3$–C$_{12}$ alkynyl, C$_3$–C$_{12}$ cycloalkyl, phenyl or phenyl substituted with 1 or 2 bromo, chloro, fluoro, C$_1$–C$_4$ alkyl, C$_1$–C$_4$ alkoxy or nitro groups; R$^5$ represents hydrogen, C$_1$–C$_{12}$ alkyl, C$_3$–C$_4$ alkenyl, C$_3$–C$_4$ alkynyl, C$_3$–C$_4$ cycloalkyl, —CN, —SO$_2$CH$_3$, OR$^7$ wherein R$^7$ is hydrogen or C$_1$–C$_4$ alkyl, —NHR$^7$, phenyl or phenyl substituted with 1 or 2 bromo, chloro, fluoro, C$_1$–C$_4$ alkyl, C$_1$–C$_4$ alkoxy or nitro group; and
R$^6$ represents hydrogen, methyl, ethyl, C$_3$ alkenyl, C$_3$ alkynyl or cyclopropyl.

The compounds of Formula I are useful in the kill and control of grassy weeds. In addition, many of the compounds of Formula I can also be employed as intermediates in the synthesis of certain of the other compounds of Formula I of the present invention.

In addition to the compounds of Formula I, compounds corresponding to the formula

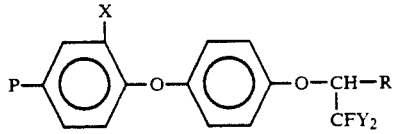

(II)

wherein P, X, Y and R$^1$ are as hereinabove defined have also been found to be useful in the same manner as those of Formula I. These compounds and their preparation are found in U.S. Pat. No. 4,107,329. Those compounds of this patent which are not specifically prepared therein can be prepared employing the appropriate starting materials and the procedures set forth therein for the corresponding compounds.

The present invention also encompasses compositions containing one or more of these active compounds as well as methods of using such compounds or compositions in the control of grassy weeds.

The active compounds of the present invention, hereinafter referred to as "active compounds" or "active ingredients", have been found to be useful as herbicides for the postermergent kill and control of undesirable vegetation, for example, grassy or graminaceous weeds.

The term "herbicide" is used herein to mean an active ingredient which controls or adversely modifies the growth of plants because of phytotoxic or other effects substantial enough to seriously retard the growth of the plant or further to damage the plant sufficiently to kill the plant.

The terms "growth controlling" or "herbicidally effective" amount are employed to designate an amount of active ingredient which causes a modifying effect and includes deviations from natural development, killing, regulation, dessication, retardation, and the like.

The term "plants" means established vegetation.

The terms "control" or "controlling" as it relates to plant growth have the same meaning as employed hereinabove for the term "herbicide".

The terms "$C_1$-$C_4$ alkyl" and "$C_1$-$C_4$ alkoxy" as employed in the present specification and claims designate alkyl or alkoxy groups, respectively, which can be straight or branched chain containing from 1 to 4 carbon atoms or cycloalkyl of 3 or 4 carton atoms.

The term "$C_1$-$C_{12}$ alkyl" as employed in the present specification and claims designates alkyl groups which can be straight or branched chain containing from 1 to 12 carbon atoms, or if so specified, can contain 1 or 2 chloro, bromo, fluoro or $C_1$-$C_4$ alkoxy groups.

The terms "$C_3$ alkenyl", "$C_3$-$C_4$ alkenyl", "$C_3$-$C_{12}$ alkenyl", "$C_3$ alkynyl", "$C_3$-$C_4$ alkynyl" and "$C_3$-$C_{12}$ alkynyl" as employed in the present specification and claims designate straight or branched chain alkenyl or alkynyl groups, respectively, containing 3, 3 or 4 or from 3 to 12 carbon atoms as indicated in said term.

The term "$C_3$-$C_{12}$ cycloalkyl" as employed in the present specification and claims designates cycloalkyl radicals or cycloalkyl radicals substituted with alkyl groups so that the total number of carbon atoms is from 3-12.

The compounds of the invention in which $R^1$ is —COOH are acidic in nature and are sometimes referred to herein as the acid form compounds. They form salts, i.e., compounds of Formula I wherein M is an agriculturally acceptable cation. These are generally alkali metal (e.g. lithium, sodium and potassium), alkaline earth metal (e.g. barium, calcium and magnesium), other metals (e.g. aluminum, zinc and iron) and ammonium salts. The particular salt chosen in any instance depends upon the particular use and upon the economics of the situation.

The ammonium salts are those salts wherein M is —N($R^8$)$_4$ wherein each $R^8$ independently represents hydrogen, $C_1$-$C_4$ alkyl, alkoxyalkyl (wherein the alkoxy and alkyl portions can each independently be straight or branched chain and contain from 1 to 4 carbon atoms), phenyl or benzyl with the proviso that only one of $R^8$ can be phenyl or benzyl.

In the present invention, it is to be noted that all substituent groups are sterically compatible with each other. The term "sterically compatible" is employed to designate substituent groups which are not affected by steric hindrance as defined in "The Condensed Chemical Dictionary", 7th edition, Reinhold Publishing Co., N.Y., page 893 (1966) which definition is as follows:

"steric hindrance. A characteristic of molecular structure in which the molecules have a spatial arrangement of their atoms such that a given reaction with another molecule is prevented or retarded in rate."

Steric hindrance may be further defined as compounds having substituents whose physical bulk does not require confinement within volumes insufficient for the exercise of their normal behavior as discussed in "Organic Chemistry" of D. J. Cram and G. Hammon, 2nd edition, McGraw-Hill Book Company, N.Y., page 215 (1964).

The active compounds of the present invention contain the optically active center

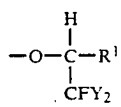

and can exist in optically active stereo isomeric forms such as the R and S enantiomeric forms. The use of the various mixtures and racemates of the above isomers are within the scope of the present invention. Additionally, the S enantiomer of such compounds have usually been found to be more active biologically than the R enantiomer and may be used whenever the greater activity justifies the extra expenses for the use of this isomer.

A general discussion of the isomer activity difference phenomenon can be found in A. Albert, Selective Toxicity, 4th edition, Met Luen & Co., Ltd., London, 1968, pp. 387-390 and more particular discussions in A. Fredga and B. Aberg, "Stereoisomerism in plant growth regulators of the auxin type", Ann. Rev. Plant Physiology 16:53-72, 1965, and in E. J. Lien, J. F. R. DeMiranda and E. J. Airens, "Quantitative structure-activity correlation of optical isomers", Molecular Pharmacology 12:598-604, 1976.

The active compounds or ingredients of the present invention are generally oils or low melting crystalline solids at ambient temperatures which are soluble in many organic solvents commonly employed as herbicidal carriers.

Representative active compounds of the present invention are set forth below in Tables 1, 2, 3, 4 and 5.

TABLE 1

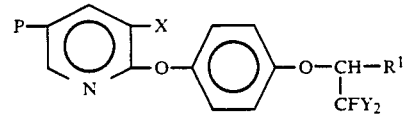
(III)

| P | X | Y | $R^1$ |
|---|---|---|---|
| —Br | —Cl | —FH | —CH$_2$OH |
| —Cl | —Cl | —H$_2$ | —CN |
| —CF$_3$ | —F | —F$_2$ | —C(O)Cl |
| —Br | —F | —F$_2$ | —C(O)Br |
| —I | —F | —F$_2$ | —C(O)H |
| —CF$_3$ | —F | —F$_2$ | —COOCH$_3$ |
| —CF$_3$ | —F | —F$_2$ | —COOC$_2$H$_5$ |
| —CF$_3$ | —Cl | —F$_2$ | —COOC$_2$H$_5$ |
| —Cl | —H | —F$_2$ | —COOH |
| —CF$_3$ | —Cl | —F$_2$ | —COON=C(CH$_3$)$_2$ |
| —CF$_3$ | —Cl | —F$_2$ | —COO-n-C$_4$H$_9$ |
| —CF$_3$ | —Br | —F$_2$ | —COONa |
| —Cl | —F | —F$_2$ | —COOH |
| —CF$_3$ | —Cl | —F$_2$ | —C(O)H |
| —I | —F | —F$_2$ | —C(O)Cl |
| —Cl | —Cl | —FH | —C(O)SCH$_3$ |
| —CF$_3$ | —Cl | —H$_2$ | 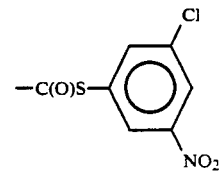 |
| —Br | —F | —F$_2$ | —C(O)NH$_2$ |
| —I | —F | —F$_2$ | —C(O)NHCH$_3$ |
| —CF$_3$ | —Cl | —F$_2$ | —C(O)N(CH$_3$)$_2$ |
| —Cl | —F | —F$_2$ | —C(O)NHNH$_2$ |

TABLE 1-continued (III)

P—[pyridine ring with X]—O—[phenyl]—O—CH(R¹)—CFY₂

| P | X | Y | R¹ |
|---|---|---|---|
| —Cl | —Cl | —F₂ | —C(O)NHOH |
| —Br | —F | —F₂ | —C(O)N(CH₂CH=CH₂)₂ |
| —CF₃ | —Cl | —F₂ | —C(O)Br |

TABLE 2

(IV)

P—[pyrimidine]—O—[phenyl]—O—CH(R¹)—CFY₂

| P | Y | R¹ |
|---|---|---|
| —CF₃ | —F₂ | —C(O)N(CH₃)₂ |
| —I | —F₂ | —C(O)Cl |
| —CF₃ | —F₂ | —C(O)SCH₃ |
| —I | —FH | —CN |
| —Br | —F₂ | —COOH |
| —CF₃ | —F₂ | —COOH |
| —CF₃ | —F₂ | —COONa |
| —Br | —F₂ | —COOCH₃ |

TABLE 3

(V)

Q—[quinoline with A]—O—[phenyl]—O—CH(R¹)—CFY₂

| A | Q | Y | R¹ |
|---|---|---|---|
| ≡CH | —F | —F₂ | —COOH |
| ≡N | —Cl | —FH | —COOCH₃ |
| ≡N | —Cl | —H₂ | —C(O)H |
| ≡N | —Cl | —F₂ | —COONa |
| ≡N | —Cl | —F₂ | —CH₂OH |
| ≡CH | —Br | —F₂ | —C(O)N(CH₃)₂ |
| ≡N | —Cl | —F₂ | —COOCH₂CH=CH₂ |
| ≡N | —Cl | —F₂ | —C(O)Cl |
| ≡N | —Cl | —F₂ | —C(O)SCH₃ |
| ≡N | —Cl | —F₂ | —COONH₄ |
| ≡N | —Cl | —F₂ | —COOH |
| ≡N | —Cl | —F₂ | —C(O)NHCN |
| ≡N | —CF₃ | —FH | —C(O)NH—⊲ |
| ≡N | —Cl | —F₂ | —C(O)NHSO₂CH₃ |
| ≡N | —Cl | —F₂ | —COO—[2,4-dichlorophenyl] |
| ≡N | —Cl | —F₂ | —COO-n-C₁₂H₂₅ |
| ≡N | —Cl | —F₂ | —COOLi |
| ≡CH | —Cl | —F₂ | —COOH |
| ≡CH | —Cl | —F₂ | —COOC₂H₅ |

TABLE 4

(VI)

G—[benzo-fused ring with L]—O—[phenyl]—O—CH(R¹)—CFY₂

| G | L | Y | R¹ |
|---|---|---|---|
| -6-CF₃ | —S— | —F₂ | —COOH |
| -6-Cl | —S— | —F₂ | —C(O)Cl |
| -6-Br | —S— | —F₂ | —COOCH₃ |
| -6-F | —S— | —F₂ | —C(O)N(CH₃)₂ |

TABLE 5

(VII)

G—[pyrido-thiazole]—O—[phenyl]—O—CH(R¹)—CFY₂

| G | Y | R¹ |
|---|---|---|
| -6-CF₃ | —F₂ | —COO-n-C₄H₉ |
| -6-Cl | —F₂ | —CN |
| -5-CF₃ | —F₂ | —COONa |
| -6-Cl | —F₂ | —C(O)SCH₃ |
| -6-Cl | —F₂ | —C(O)N(CH₃)₂ |

The preferred compounds of the present invention include those compounds of Formula 1 wherein Ar is as follows:

5-chloro-2-pyridyl
5-trifluoromethyl-2-pyridyl
3,5-dichloro-2-pyridyl
3-chloro-5-trifluoromethyl-2-pyridyl
3-fluoro-5-trifluoromethyl-2-pyridyl
5-chloro-3-fluoro-2-pyridyl
6-chloro-2-quinolinyl
6-fluoro-2-quinolinyl
6-chloro-2-quinoxalinyl
6-fluoro-2-quinoxalinyl
6-chloro-2-benzothiazolyl
6-chloro-2-benzoxazolyl
5-chloro-2-thiazolylopyridyl
5-fluoro-2-thiazolopyridyl.

The active ingredients wherein R¹ is —COOH constitute a preferred embodiment and active ingredients wherein R¹ is —COOR² constitute a further preferred embodiment.

The active ingredients of the above Formula I can be prepared in accordance with one or more of the following procedures.

The compounds of the present invention are prepared employing a variety of procedures.

The compounds wherein —CFY₂ is —CF₃, R¹ is —COOR² and R² is C₁-C₁₂ alkyl (R⁹) are prepared employing a multi-step procedure which can be represented as follows:

Step 1

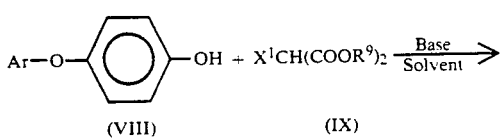

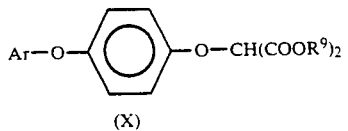

Step 2

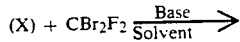

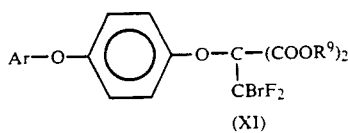

Step 3

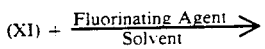

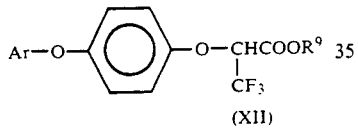

No attempt is made to present a balanced equation. In the above formulae, Ar, $X^1$, and $R^9$ are as defined hereinabove.

In carrying out the first step of this procedure, the appropriate phenol of Formula IX is reacted with an appropriate dialkylhalomalonate of Formula IX in the presence of a base and an inert, polar solvent at a temperature of from 25°–100° C. The base should be non-nucleophilic and strong enough to deprotonate the phenol. Representative bases include, for example, sodium hydride and potassium carbonate. Representative solvents which can be employed include acetonitrile, dimethylformamide (DMF), dimethyl sulfoxide (DMSO), acetone, tetrahydrofuran (THF) and the like. The desired dialkyl ester product of Formula X is recovered employing conventional procedure.

In the second step, the dialkyl ester of Formula X is reacted under anhydrous conditions and in a sealed reaction vessel with dibromodifluoromethane ($CF_2Br_2$) at room temperature in the presence of an excess (5%) of a strong but non-nucleophilic base and an inert, dipolar, aprotic solvent. Representative bases include sodium hydride and potassium carbonate, Representative solvents include, for example, DMF, THF, DMSO and the like. The reaction is slow and usually requires from 2 to 4 days for completion. A fairly large excess (2 to 4x) of the $CF_2Br_2$ is usually employed. The thus formed 2-(bromodifluoromethyl)propandioic acid: dialkyl ester product of Formula XI is recovered by the use of conventional separatory procedures.

In step three, the dialkyl ester of Formula XI is reacted under anhydrous conditions at temperatures of from about 120° to 170° C. with a nucleophilic fluorinating agent in the presence of DMSO. Representative fluorinating agents include cesium fluoride and potassium fluoride. The desired trifluoropropionate product of Formula XI is obtained employing either distillation or chromatographic purification procedures. The products are either oils or low melting solids.

In an alternative procedure employing a reaction procedure taught in U.S. Pat. No. 4,107,329, incorporated herein by reference, the compounds of Formula XII wherein $-CFY_2$ is $-CF_3$, $R^1$ is $-COOR^2$ and $R^2$ is $R^9$ can be prepared by the reaction of (aryloxy)-phenyliodonium salt of the formula

with an alkali metal salt of 2-hydroxy-3,3,3-(trifluoromethyl)propionate, corresponding to the formula

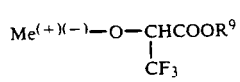

wherein Ar, $X^1$ and $R^9$ are as hereinbefore defined, and Me is sodium or potassium.

The reaction is conveniently carried out by contacting the compounds of Formulae XIII and XIV neat or in the presence of a solvent at temperatures from ambient to about 50° C. or more. Representative solvents include toluene, xylene and the like.

The compounds of Formula XII wherein $-CFY_2$ is $-CH_2F$ or $-CHF_2$ can be prepared employing a multistep procedure which can be represented as follows:

Step 1

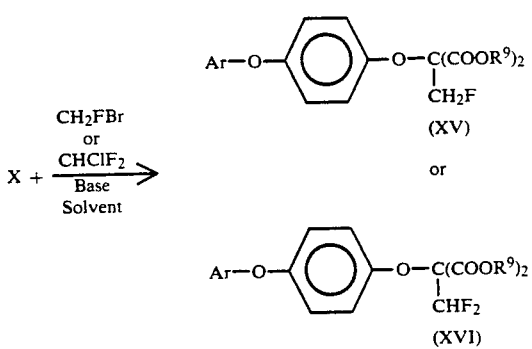

Step 2

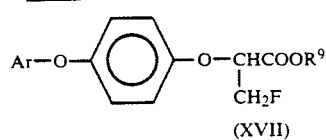
(XVII)

XV or XVI + $\xrightarrow{H_2SO_4}$ or

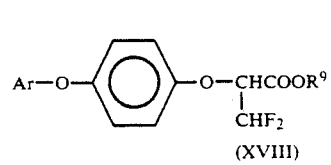
(XVIII)

No attempt is made to present a balanced equation. In the above formulae, Ar and $R^9$ are as defined hereinabove.

In carrying out Step 1, an appropriate dialkyl ester of Formula X (prepared as set forth hereinbefore) is reacted, at room temperature and under anhydrous conditions, and in a sealed reaction vessel with either bromofluoromethane ($CH_2FBr$) or chlorodifluoromethane ($CHClF_2$), depending upon the final product desired, in the presence of a strong but non-nucleophilic base and an inert, dipolar, aprotic solvent. Representative bases include sodium hydride and potassium carbonate. Representative solvents include, for example, DMF, THF, DMSO and the like. It is preferred that the reaction be conducted in a closed system to prevent the loss of the gaseous halide reactants. The thus formed 2-(fluoromethyl(or difluoromethyl)) propandioic acid dialkyl ester product of Formula XV (or XVI) is recovered by the use of conventional separatory procedures.

In step two, the dialkyl ester of Formula XV (or XVI) is hydrolyzed and decarboxylated employing a strong acid such as concentrated sulfuric acid. This step is conducted employing conventional conditions. The products can be recovered employing conventional separatory procedures.

The ester compounds wherein $R^2$ is other than $C_1$–$C_4$ alkyl can conveniently be prepared by a variety of procedures. Such procedures and the specific procedure to employ when preparing specific esters are well known to those skilled in the art. Techniques of conventional ester exchange, ester formation from the reaction of the free acid or the acid halide with an appropriate alcohol are some of the known procedures. These and others are exemplified in Wagner et al., "Synthetic Organic Chemistry", John Wiley & Sons, N.Y. (1953) pages 480-499. These pages and the references cited therein are incorporated herein by reference thereto.

The free acid compounds, i.e., where $H^1$ is —COOH can also be prepared from the corresponding ester compound by employing conventional procedures wherein the ester is hydrolyzed with an acid such as sulfuric or hydrochloric acid. Such procedures are well known.

Those compounds, wherein $R^1$ is —COOM, are conveniently prepared employing conventional hydrolysis procedures. In one such procedure, the ester product is reacted with an aqueous base such as, for example, aqueous sodium or potassium hydroxide in an inert solvent such as, for example, aqueous methanol or ethanol. The hydrolysis is conveniently carried out at room temperature for a period of from 1½ hours to 3 days or more.

In an alternative procedure, those compounds wherein $R^1$ is —COOM are conveniently prepared by reacting the free acid compound, i.e., where $R^1$ is —COOH with an aqueous metal hydroxide or carbonate (MOH or $M_2CO_3$ wherein M is as hereinbefore defined) employing conventional reaction procedures and conditions.

Those compounds wherein $R^1$ is $$-\overset{O}{\underset{\|}{C}}X^1$$

and $X^1$ is as hereinbefore defined can be conveniently prepared employing conventional procedures for preparing acyl halides from carboxylic acids. In one such procedure, thionyl chloride is reacted with the free acid, i.e., compounds wherein $R^1$ is —COOH, at room temperature or under gentle reflux in the presence of a solvent such as xylene or toluene.

The compounds wherein $R^1$ is $$-\overset{O}{\underset{\|}{C}}-NR^4R^5$$

can be prepared by the reaction of the acid halide with aqueous ammonia, or aqueous monoalkyl or dialkylamine in the presence of a solvent such as ether, methylene chloride, acetonitrile or the like at a temperature of from 0° up to reflux.

The compounds wherein $R^1$ is —$CH_2OH$ can be prepared employing known procedures including reducing carboxylic acids, their esters or acid chlorides to the corresponding alcohol. Such procedures are discussed in Wagner et al. cited surpa. pages 155°-158.

The compounds wherein $R^1$ is —C(O)H can be prepared employing known procedures including the catalytic dehydrogenation of the corresponding alcohol ($R^1$=—$CH_2OH$); the controlled oxidation of said alcohol; or the selective catalytic reduction of the corresponding acyl chloride. Such procedures are discussed in Wagner et al., cited supra, pages 289-290.

The compounds wherein $R^1$ is —CN can be prepared employing known procedures including dehydration of the corresponding amide, and the treatment of the free acid with p-toluenesulfonamide and phosphorus pentachloride. Such procedures are discussed in Wagner et al., cited supra, pages 596-597.

The compounds wherein $R^1$ is —C(O)$SR^4$ can be prepared employing various known procedures including the reaction of the corresponding acyl chloride with an appropriate mercaptan; treatment of the free acid with an appropriate mercaptan or trisalkylthioborane in the presence of either polyphosphate ester or phenyl dichlorophosphate; or by the treatment of the ester ($R^1$ is —$COOR^2$) with an appropriate trimethylsilyl sulfide (($CH_3)_3SiSR^4$) and aluminum chloride. These procedures are discussed in March, "Advanced Organic Chemistry-Reactions, Mechanisms, and Structure"; John Wiley & Sons, N.Y. (1985) pages 362-363.

The desired product can be separated from the reaction product of the above preparative procedures employing conventional separatory procedures known to those skilled in the art including steps of solvent extraction, filtration, water washing, column chromatography, neutralization, acidification, crystallization and distillation.

The optical isomer forms of the active compounds of the present invention can be prepared employing well known conventional procedures. In one such procedure, the free acid is reacted with an optically active amine to prepare the amine salt. The thus formed diastereoisomers are then separated from each other employing chromatographic techniques or crystallization procedures. The optically active free acid can be obtained by conventional hydrolysis. The optically active derivatives of the acid can then be prepared employing the same procedures employed to prepare the racemic mixtures set forth hereinabove.

Since the hereinabove and hereinafter set forth compounds preparation procedures employ only standard chemistry practices, and it is known that slightly different reactants can require slightly different reaction parameters from those for other reactants, it is to be understood that minor modifications to the reaction parameters set forth such as the use of an excess of one reactant, the use of a catalyst, the use of high temperature and/or pressure equipment, high speed mixing the other such conventional changes are within the scope of this invention.

PREPARATION OF STARTING MATERIALS

The 4-(aryloxy)phenols employed herein as starting materials and corresponding to the formula

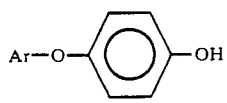

(VIII)

are well known compounds in the chemical literature. Teachings thereof can be found, for example, in European Patent publications 0171724 and 0148119 and in U.S. Pat. Nos. 4,266,063; 4,267,317 and 4,414,398.

Additionally, compounds of the formula

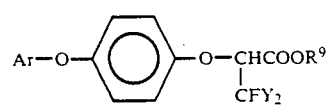

(XIX)

wherein Ar, Y and $R^9$ are as hereinbefore defined, can be prepared by the reaction of an appropriate arylhalide corresponding to the formula $Ar-X^2$ (XX)

wherein Ar is as hereinbefore defined and $X^2$ represents —Br, —Cl or —F and appropriate hydroxyphenoxy alkyl carboxylic acid ester corresponding to the formula

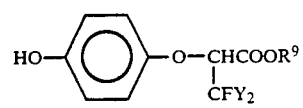

(XXI)

wherein $Y^2$ and $R^9$ are as hereinbefore defined. In carrying out this reaction, the reactants and a strong base such as an anhydrous alkali metal hydride, alkoxide, hydroxide or carbonate are mixed together in a dipolar, aprotic solvent such as, for example, dimethylformamide (DMF), acetone, methyl ethyl ketone, acetonitrile, dimethylsulfoxide (DMSO), sulfolane, N-methylpyrrolidone or the like. The reaction is advantageously carried out at elevated temperatures of from about 50° to 120° C.

The hydroxyphenoxy alkanoic carboxylic acid esters corresponding to the formula

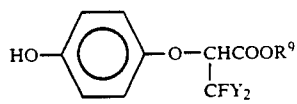

(XXI)

are prepared by a variety of procedures.

The compounds are preferably prepared employing a multi-step procedure similar to those employed in preparing compounds of Formula XII, XVII and XVIII. The procedure can be represented as follows:

Step 1

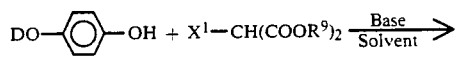

(XXII)

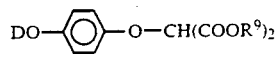

(XXIII)

Step 2

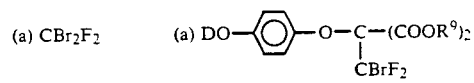

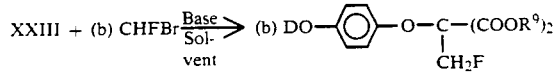

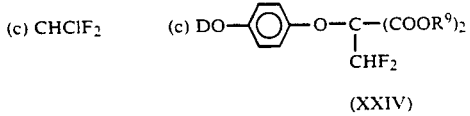

(XXIV)

Step 3-a

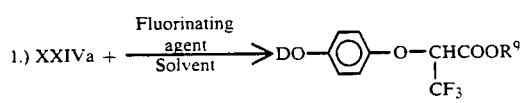

(XXVa)

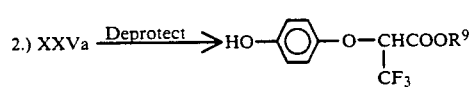

(XXIa)

Step 3-b/c

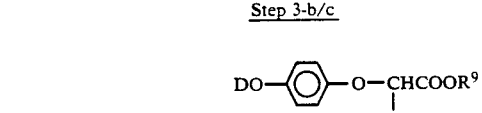

(XXVb)

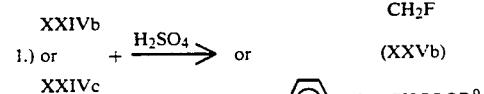

(XXVc)

-continued

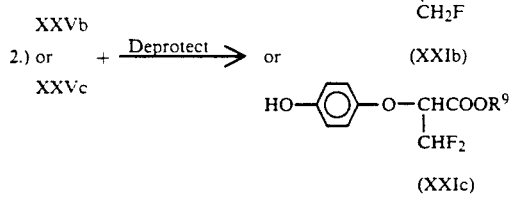

XXVb
2.) or + Deprotect → or (XXIb)
XXVc or (XXIc)

No attempt was made to present a balanced equation. In the above formulae, $X^1$ and $R^9$ are as hereinbefore defined, and D is a protecting group as hereinafter defined.

In the above formulae, the compounds of Formula XXI, wherein $-CFY_2$ is $-CF_3$ is set forth as XXIa; the compound wherein $-CFY_2$ is $-CH_2F$ is set forth as XXIb and the compound wherein $-CFY_2$ is $-CHF_2$ is set forth as XXIc. This same listing is employed for compounds of Formulae XXIV and XXV.

The above reaction steps can be carried out as follows:

Step 1

Substantially equimolar amounts of hydroquinone of Formula XXII which contains a protecting group (D) and an appropriate dialkylhalomalonate of Formula IX are reacted under the same reaction conditions employed hereinabove in preparing the compounds of Formula X.

Protecting groups and their use in reactions involving hydroquinone compounds are well known to those skilled in the art. Such usage is taught in "Protective Groups in Organic Synthesis" by T. W. Greene; Chapter 3, *Protection For Phenols and Catechols;* John Wiley & Sons, N.Y., N.Y.; (1981), which is being incorporated herein by reference thereto. The specific protecting group employed is not critical, any of the conventionally employed protecting groups can be employed herein as long as this group is not reactive with the dialkylhalomalonate. Representative groups include $-CH_3$, $-CH_2OCH_3$, $-CH_2OCH_2CH_2OCH_3$ and the like.

Step 2

In the second step the dialkyl ester of Formula XXIII is reacted under anhydrous conditions and in a sealed reactor with either a) dibromodifluoromethane; b) bromofluoromethane; or c) chlorodifluoromethane depending upon whether the radical $-CFY_2$ in the compound of Formula XXI is $-CF_3$, $-CH_2F$ or $-CHF_2$. This reaction is carried out employing the reaction procedures and conditions employed hereinabove in preparing the compounds of Formulae XI, XV and XVI.

Step 3-a

In this step, the dialkyl ester of Formula XXV(a) is reacted under anhydrous conditions with a nucleophilic fluorinating agent in the presence of DMSO. This reaction is carried out employing the reaction conditions and procedures employed to prepare the compounds of Formula XI.

The above product is then deprotected employing a variety of techniques depending upon the nature of the protecting group. The above cited Greene reference describes such techniques. As one example, the above product where D is $-CH_2OCH_3$ is mixed with an alcoholic solvent and a catalytic amount of a strong acid and refluxed for up to 24 hours to convert the product to the desired hydroxy compound. Representative acids include p-toluenesulfonic acid, and the like. The product is thereafter recovered employing conventional procedures of solvent evaporation, solvent extraction and the like.

Step 3-b/c the dialkyl ester of Formulae XXIVb or c is hydrolyzed and decarboxylated employing a strong acid. This reaction is carried out employing the procedures and conditions employed hereinabove to prepare the compounds of Formulae XVII or XVIII.

The above products are then deprotected as set forth hereinabove to prepare the compound of Formula XXIa. In some situations, depending on the specific protection group, the strong acid used above to hydrolyze and decarboxylate the ester of Formula b or c may also deprotect in situ.

In addition, those compounds not specifically taught or produced can be prepared by procedures analogous to those employed to prepare the taught or produced compounds employing the appropriate starting materials.

The aromatic/heterocyclic halides employed as starting materials and which correspond to the formula $$Ar-X^2 \qquad (II)$$

wherein Ar and $X^2$ are as hereinbefore defined, are all known and/or commercially produced compounds and, for the most part, are taught in the above-listed applications and/or patents which teach preparing compounds of Formulae VIII and XIII. In addition, compounds of Formula XX not specifically taught can be prepared by procedures analogous to those of the above references employing the appropriate starting materials.

The following examples illustrate the present invention and the manner by which it can be practiced but, as such, as not to be construed as limitations upon the overall scope thereof.

The compounds obtained in the following examples were generally characterized by infrared and nuclear magnetic resonance spectrometry.

EXAMPLE I

Ethyl 2-(4-((3-chloro-5-(trifluoromethyl)-2-pyridinyl)oxy)-phenoxy)-3,3,3-trifluoropropionate (Compound I)

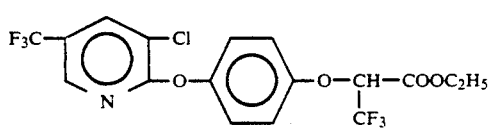

The title compound was prepared employing the following three steps.

Step A 2-(4-((3-Chloro-5-(trifluoromethyl)-2-pyridinyl)oxy)-phenoxy) 1,3-propandioic acid:diethyl ester (Compound A)

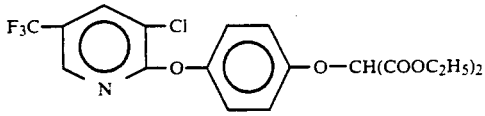

A mixture of 1.45 grams (g) (5 millimole (mmol)) of 4-((3-chloro-5-(trifluoromethyl)-2-pyridinyl)oxy)-phenol, 0.76 g (5.5 mmol) of anhydrous, powdered potassium carbonate, 50 milliliters (ml) of acetonitrile and 1.07 g (5.5 mmol) of diethyl chloromalonate was stirred under a nitrogen atmosphere at room temperature for 24 hours. The reaction mixture was then poured into water and extracted with two portions of ether. The combined organic layers were washed with 2 percent aqueous NaOH, then with water, dried over MgSO4 and evaporated to dryness. The residual solid was recrystallized from hexane to give 1.74 g (78 percent of theoretical) of Compound A as colorless crystals melting at 129°–132° C.

| Elemental Analysis: | % C | % H | % N |
|---|---|---|---|
| Calculated for $C_{19}H_{17}ClF_3NO_5$: | 50.96 | 3.83 | 3.13 |
| Found: | 50.88 | 3.89 | 3.13 |

Step B 2-(Bromodifluoromethyl)-2-(4-((3-chloro-5-(trifluoromethyl)-2-pyridinyl)oxy)phenoxy)propandioic acid:diethyl ester (Compound B)

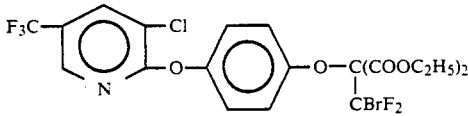

A nitrogen flushed flask was charged with 15 ml of hexane and 0.44 g (11 mmol) of 60 percent NaH/oil dispersion and stirred for 5 minutes. The hexane was decanted from the mixture and replaced with 75 ml of dry DMF. To this mixture was slowly added 4.48 g (10 mmol) of Compound A, and the resulting mixture stirred at room temperature until gas evolution had ceased (~2 hours). The mixture was cooled in an ice bath, and 5 ml (55 mmol) of dibromodifluoromethane was added in one portion. The flask was tightly stoppered and allowed to stir at room temperature for 48 hours. At this point the mixture was cooled in an ice bath and quenched by cautious addition of 2 ml of acetic acid followed by dropwise addition of water. The mixture was then poured into water and extracted with three portions of ether. The combined organic layers were washed with saturated aqueous NaHCO3, dried over MgSO4 and evaporated to leave an oil. The desired product (Compound B) was separated from unreacted starting material by preparative scale HPLC, eluting with 19:1 hexane:ethyl acetate and, after removal of solvent, dried at 75° C. and 0.05 mm Hg for 2 hours. This left 2.72 g (47 percent) of Compound B as a pale yellow oil. The product was identified on the basis of its corresponding IR and $^1H$ and $^{19}F$ NMR spectra.

| Elemental Analysis: | % C | % H | % N |
|---|---|---|---|
| Calculated for $C_{20}H_{16}BrClF_5NO_6$: | 41.65 | 2.80 | 2.43 |
| Found: | 42.06 | 2.74 | 2.41 |

Step C

Title Compound (Compound I)

A mixture of 1.65 g (2.9 mmol) of Compound B 0.88 g (5.8 mmol) of cesium fluoride and 20 ml of DMSO was warmed under a nitrogen atmosphere at 135° C. for 2 hours. The mixture was cooled to room temperature and poured into water and the resulting aqueous mixture extracted with three portions of ether. The combined organic layers were washed twice with water and then filtered through a short column of silica gel eluting with 1:1 hexane:ethyl acetate. After removal of solvent the residual oil was separated from by-products by preparative scale HPLC, eluting with 94:6 hexane:ethyl acetate. The sample was dried at 77° C. under aspirator vacuum for 2.5 hours to leave 0.132 g of the title compound as a pale yellow oil. The product was identified on the basis of its corresponding IR and $^1H$ and $^{19}F$ NMR spectra.

| Elemental Analysis: | % C | % H | % N |
|---|---|---|---|
| Calculated for $C_{17}H_{12}BrClF_6NO_4$: | 46.01 | 2.73 | 3.16 |
| Found: | 47.43 | 2.73 | 3.30 |

EXAMPLE II

Ethyl 2-(4-((3-fluoro-5-(trifluoromethyl)-2-pyridinyl)oxy)-phenoxy)-3,3,3-trifluoropropionate (Compound II)

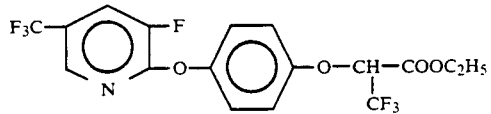

The title compound was prepared employing the following three steps.

Step A 2-(4-((3-Fluoro-5-(trifluoromethyl)-2-pyridinyl)oxy)-phenoxy)propandioic acid:diethylester (Compound C)

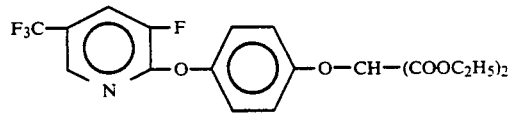

A mixture of 13.65 g (50 mmol) of 4-((3-fluoro-5-(trifluoromethyl)-2-pyridinyl)oxy)phenol, 7.59 g (55 mmol) of anhydrous, powdered potassium carbonate, 10.70 g (50 mmol) of diethyl chloromalonate and 200 ml of acetonitrile was warmed at reflux for a period of 4 hours. The reaction mixture was cooled and poured into water and the aqueous mixture extracted with two portions of ether. The combined organic layers were washed with two portions of 2 percent aqueous NaOH, then with water, dried over MgSO₄ and evaporated to dryness. The residual oil was purified by preparative scale HPLC, eluting with 17:3 hexane:ethyl acetate and then crystallized from hexane to give 12.64 g (59 percent) of Compound C as colorless crystals, melting at 51°–54° C.

| Elemental Analysis: | % C | % H | % N |
|---|---|---|---|
| Calculated for C$_{19}$H$_{17}$F$_4$NO$_6$: | 52.90 | 3.97 | 3.25 |
| Found: | 52.88 | 3.93 | 3.29 |

Step B 2-(Bromodifluoromethyl-2-(4-((3-fluoro-5-trifluoromethyl)-2-pyridinyl)oxy)phenoxy)propandioic acid:diethyl ester (Compound D)

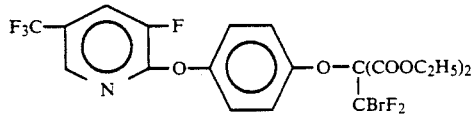

A nitrogen flushed flask was charged with 20 ml of hexane and 1.16 g (29 mmol) of 60 percent NaH/oil dispersion and the mixture stirred for 5 minutes. The hexane was decanted from the solid and replaced with 125 ml of dry DMF. To this mixture was slowly added, in portions, 11.21 g (26 mmol) of Compound C and the mixture stirred at room temperature for 1 hour. The resulting mixture was cooled in an ice bath, and 8 ml (88 mmol) of dibromodifluoromethane was added in one portion. The flask was tightly stoppered and the mixture stirred at room temperature for 4 days. The mixture was cooled in an ice bath, quenched by cautious addition of 2 ml of acetic acid followed by dropwise addition of water and then poured into water. The aqueous mixture was extracted with three portions of ether and the combined organic layers washed with saturated aqueous NaHCO₃ and two portions of water, dried over MgSO₄ and evaporated to dryness. The residual oil was separated from some unreacted starting material by preparative scale HPLC, eluting with 9:1 hexane: ethyl acetate, and then dried at 55° C. and 0.05 mm Hg for 1.5 hours to leave 7.47 g (51 percent) of Compound D as a colorless oil, n$^{25}$/D=1.4861. The product was identified on the basis of its corresponding IR and ¹H and ¹⁹F NMR spectra.

| Elemental Analysis: | % C | % H | % N |
|---|---|---|---|
| Calculated for C$_{20}$H$_{16}$BrF$_6$NO$_6$: | 42.87 | 2.88 | 2.50 |
| Found: | 43.22 | 2.80 | 2.70 |

Title Compound (Compound II)

A mixture of 4.48 g (8 mmol) of Compound D 2.43 g (16 mmol) of cesium fluoride and 40 ml of DMSO was warmed at 135° C. for a period of 2 hours. The mixture was cooled to room temperature, poured into dilute aqueous HCl and extracted with the three portions of ether. The combined organic layers were washed with water, 2 percent aqueous NaOH and again with water, dried over MgSO₄ and then filtered through a short column of silica gel, eluting with methylene chloride. After removal of solvent, the residue was separated from by-products by preparative scale HPLC, eluting with 94:6 hexane:ethyl acetate. The product was dried at 75° C. and 0.1 mm Hg for 4 hours to leave 0.58 g (17 percent) of the title compound as a pale yellow oil. The product was identified on the basis of its corresponding IR and ¹H and ¹⁹F NMR spectra.

| Elemental Analysis: | % C | % H | % N |
|---|---|---|---|
| Calculated for C$_{17}$H$_{12}$F$_7$NO$_4$: | 47.78 | 2.83 | 3.28 |
| Found: | 48.60 | 2.28 | 3.33 |

The compounds of the present invention have been found to be suitable for use in methods for the selective postemergent control of many annual and perennial grassy weeds.

For such uses, unmodified active ingredients of the present invention can be employed. However, the present invention also embraces the use of the active compounds in admixture with inert materials, known in the art as agricultural adjuvants and/or carriers, in solid or liquid form. Thus, for example, an active ingredient can be dispersed on a finely-divided solid and employed therein as a dust or granule. Also, the active ingredients, as liquid concentrates or solid compositions comprising one or more of the active ingredients can be dispersed in water, typically with aid of a wetting agent, and the resulting aqueous dispersion employed as a spray. In other procedures, the active ingredients can be employed as a constituent of organic liquid compositions, oil-in-water and water-in-oil emulsions or water dispersions, with or without the addition of wetting, dispersing, or emulsifying agents. Suitable adjuvants of the foregoing type are well known to those skilled in the art.

The herbicidally effective concentration of the active ingredients in solid or liquid compositions generally is from about 0.0003 to about 95 percent by weight or more. Concentrations from about 0.05 to about 50 percent by weight are often employed. In compositions to be employed as concentrates, the active ingredient can be present in a concentration from about 5 to about 98 weight percent. The active ingredient compositions can also contain other compatible additaments, for example, phytotoxicants, plant growth regulators and other biologically active compounds used in agriculture.

In further embodiments, the compounds of the present invention or compositions containing the same, can be advantageously employed in combination with one or more additional pesticidal compounds. Such additional pesticidal compounds may be insecticides, nematocides, miticides, arthropodicides, herbicides, fungicides or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use or as an additament. The compounds in combination can generally be present in a ratio of from 1 to 100 parts of the compound of the present invention with from 100 to 1 part of the additional compound(s).

The active ingredients of the present invention have been found to possess desirable postemergent activity against grassy weeds such as green and giant foxtail, barnyard grass, wild oats and crabgrass. These compounds are also uniquely effective in controlling perennial grassy weeds such as Johnson grass, quackgrass, and bermuda grass.

The exact amount of the active material to be applied is dependent not only on the specific active ingredient being applied, but also on the particular action desired, the weed plant species to be controlled and the stage of growth thereof as well as the part of the plant to be contacted with the toxic active ingredient.

In the present postemergent operations, a dosage of about 0.01 to about 20 lbs/acre (0.056-22.4 kg/hectare) is generally applicable, although not all compounds are equally effective and some weeds are more difficult to control. Thus, a dosage rate in the range of about 0.05 to about 1.0 lb/acre (0.01-1.12 kg/hectare) is preferred in postemergent control of annual grassy weeds, while about 0.05 to about 5 lbs/acre (0.056-5.6 kg/hectare) is a preferred dosage range for the postemergent control of perennial grassy weeds.

The following examples illustrate the effects of the compounds of this invention.

EXAMPLE III

Representative compositions of the present invention were evaluated to determine their effectiveness in postemergent operations.

Aqueous dispersions were prepared by admixing predetermined amounts of one of the hereinafter set forth compounds, dissolved in a predetermined amount of an inert solvent, with a predetermined quantity of water and a predetermined amount of a surfactant to give aqueous dispersions of one of compounds I or II as the sole toxicant.

Seeds of various plant species were planted in beds of good agricultural soil and growth in a greenhouse. After the plants had emerged and had grown to a height of from 2-8 inches (depending on the plant species), separate beds of the plants were sprayed to runoff with one of the above-prepared compositions at a predetermined treating rate (in parts of the active compound per million parts of the ultimate composition (PPM)). Other beds of the plants were sprayed with a water-surfactant mixture, containing no active compound, to serve as controls. After treatment, the beds were maintained for two weeks under greenhouse conditions conductive for good plant growth. At the end of this period, the beds were examined to determine the amount of kill and control. The specific plant species, test compounds and the percent postemergent control are set forth below in Table 6.

TABLE 6

| Compound No. Tested | Treatment Rate in PPM | Percent Kill and Control of the Following Plant Species | | | | |
|---|---|---|---|---|---|---|
| | | Barn- yard- grass | Crab- grass | John- son Grass | Wild Oats | Green Foxtail |
| 1 | 1000 | 100 | 100 | 100 | NT | 100 |
| | 500 | 100 | 100 | 100 | NT | 100 |
| | 250 | 100 | 100 | 100 | NT | 85 |
| | 125 | 80 | 100 | 100 | NT | 100 |
| 2 | 1000 | 100 | 100 | 100 | 100 | 100 |
| | 500 | 100 | 100 | 100 | 100 | 100 |
| | 250 | 100 | 100 | 100 | 100 | 100 |
| | 125 | 100 | 100 | 100 | 10 | 98 |

What is claimed is:

1. A compound or an optical isomer thereof corresponding to the formula

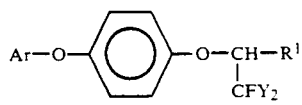

wherein
Ar represents

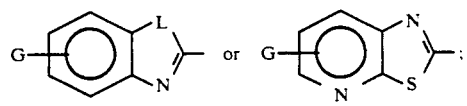

each Y independently represents —H or —F;
G represents, in the 5 or 6 ring position, —Br, —Cl, —F or —CF$_3$;
R$^1$ represents —CH$_2$OH, —CN, —COOH, —COOM —COOR$^2$,

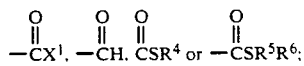

X$^1$ represents —Br or —Cl;
L represents oxygen or sulfur;
M represents an agriculturally acceptable cation;
R$^2$ represents C$_1$-C$_{12}$ alkyl, C$_3$-C$_{12}$ alkenyl, C$_3$-C$_{12}$ alkynyl, C$_3$-C$_{12}$ cycloalkyl, C$_1$-C$_{12}$ alkyl substituted with 1 or 2 bromo, chloro, fluoro or C$_1$-C$_4$ alkoxy substituents or R$^2$ represents phenyl substituted with 1 or 2 bromo, chloro, fluoro, C$_1$-C$_4$ alkyl, C$_1$-C$_4$ alkoxy or nitro substituents or R$^2$ represents the radical —N=C(R$^3$)$_2$ wherein each R$^3$ independently represents a C$_1$-C$_4$ alkyl;
R$^4$ represents C$_1$-C$_{12}$ alkyl, C$_3$-C$_{12}$ alkenyl, C$_3$-C$_{12}$ alkynyl, C$_3$-C$_{12}$ cycloalkyl phenyl or phenyl substituted with 1 or 2 bromo, chloro, fluoro, C$_1$-C$_4$ alkyl, C$_1$-C$_4$ alkoxy or nitro groups;
R$^5$ represents hydrogen, C$_1$-C$_{12}$ alkyl, C$_3$-C$_4$ alkenyl, C$_3$-C$_4$ alkynyl, C$_3$-C$_4$ cycloalkyl, —CN —SO$_2$CH$_3$, —OR$^2$ wherein R$^7$ is hydrogen or C$_1$-C$_4$ alkyl, —NHR$^7$, phenyl or phenyl substituted with 1 or 2 bromo, chloro, fluoro, C$_1$-C$_4$ alkyl, C$_1$-C$_4$ alkoxy or nitro groups; and
R$^6$ represents hydrogen, methyl, ethyl, C$_3$ alkenyl, C$_3$ alkynyl or cyclopropyl.

2. A compound as defined in claim 1 which is in the S enantiomeric isomer form.

3. A compound as defined in claim 1 wherein Ar is

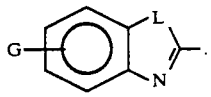

4. A compound as defined in claim 1 wherein Ar is

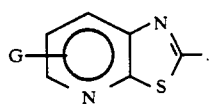

5. A composition which comprises an agriculturally acceptable inert adjuvant in intimate admixture with a herbicidally effective amount of a compound, as the active material, which corresponds to the formula

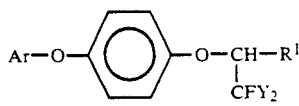

wherein
Ar represents

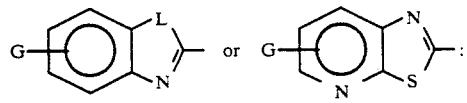

each Y independently represents —H or —F;
G represents, in the 5 to 6 ring position, —Br, —Cl, —F, or —CF$_3$;
R$^1$ represents —CH$_2$OH, —CN, —COOH, —COOM, —COOR$^2$,

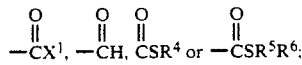

X$^1$ represents —Br or —Cl;
L represents oxygen or sulfur;
M represents an agriculturally acceptable cation;
R$^2$ represents C$_1$-C$_{12}$ alkyl, C$_3$-C$_{12}$ alkenyl, C$_3$-C$_{12}$ alkynyl, C$_3$-C$_{12}$ cycloalkyl, C$_1$-C$_{12}$ alkyl substituted with 1 or 2 bromo, chloro, fluoro or C$_1$-C$_4$ alkoxy substituents or R$^2$ represents phenyl substituted with 1 or 2 bromo, chloro fluoro, C$_1$-C$_4$ alkyl, C$_1$-C$_4$ alkoxy or nitro substituents or R$^2$ represents the radical —N=C(R$^3$)$_2$ wherein each R$^3$ independently represents a C$_1$-C$_4$ alkyl;
R$^4$ represents C$_1$-C$_{12}$ alkyl, C$_3$-C$_{12}$ alkenyl, C$_3$-C$_{12}$ alkynyl, C$_3$-C$_{12}$ cycloalkyl, phenyl or phenyl substituted with 1 or 2 bromo, chloro, fluoro, C$_1$-C$_4$ alkyl, C$_1$-C$_4$ alkoxyl or nitro groups:
R$^5$ represents hydrogen, C$_1$-C$_{12}$ alkyl, C$_3$-C$_4$ alkenyl, C$_3$-C$_4$ alkynyl, C$_3$-C$_4$ cycloalkyl, —CN, —SO$_2$CH$_3$, —OR$^7$ wherein R$^7$ is hydrogen or C$_1$-C$_4$ alkyl, —NHR$^7$, phenyl or phenyl substituted with 1 or 2 bromo, chloro, fluoro, C$_1$-C$_4$ alkyl, C$_1$-C$_4$ alkoxy or nitro groups; and
R$^6$ represents hydrogen, methyl, ethyl, C$_3$ alkenyl, C$_3$ alkynyl or cyclopropyl.

6. A composition as defined in claim 5 wherein the compound is in the S enantiomeric isomer form.

7. A composition as defined in claim 5 wherein Ar is

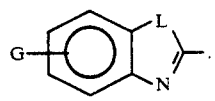

8. A composition as defined in claim 5 wherein Ar is

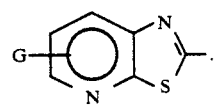

9. A method for the postemergent kill and control of grassy weeds which comprises applying to said weeds a herbicidally effective amount of a composition comprising an agriculturally acceptable inert adjuvant in intimate admixture with, as the active material, a compound corresponding to one of the formulae

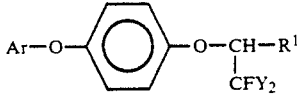

wherein
Ar represents

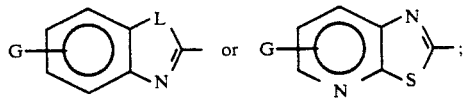

each Y independently represents —H or —F;
G represents, in the 5 or 6 ring position, —Br, —Cl, —F or —CF$_3$;
R$^1$ represents —CH$_2$OH, —CN, —COOH, —COOM, —COOR$^2$,

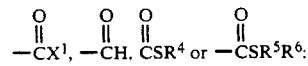

X$^1$ represents —Br or —Cl;
L represents oxygen or sulfur;
M represents an agriculturally acceptable cation;
R$^2$ represents C$_1$-C$_{12}$ alkyl, C$_3$-C$_{12}$ alkenyl, C$_3$-C$_{12}$ alkynyl, C$_3$-C$_{12}$ cycloalkyl, C$_1$-C$_{12}$ alkyl substituted with 1 or 2 bromo, chloro, fluoro or C$_1$-C$_4$ alkoxy substituents or R$^2$ represents phenyl substituted with 1 or 2 bromo, chloro fluoro, C$_1$-C$_4$ alkyl, C$_1$-C$_4$ alkoxy or nitro substituents or R$^2$ represents the radical —N=C(R$^3$)$_2$ wherein each R$^3$ independently represents a C$_1$-C$_4$ alkyl;
R$^4$ represents C$_1$-C$_{12}$ alkyl, C$_3$-C$_{12}$ alkenyl, C$_3$-C$_{12}$ alkynyl, C$_3$-C$_{12}$ cycloalkyl, phenyl or phenyl substituted with 1 or 2 bromo, chloro, fluoro, C$_1$-C$_4$ alkyl, C$_4$-C$_4$alkoxy or nitro groups;
R$^5$ represents hydrogen, C$_1$-C$_{12}$ alkyl, C$_3$-C$_4$ alkenyl, C$_3$-C$_4$ alkynyl, C$_3$-C$_4$ cycloalkyl, —CN, —SO$_2$CH$_3$, —OR$^7$ wherein R$^7$ is hydrogen or C$_1$-C$_4$ alkyl, —NHR$^7$, phenyl or phenyl substituted with 1 or 2 bromo, chloro, fluoro, C$_1$-C$_4$ alkyl, C$_1$-C$_4$ alkoxy or nitro groups; and R$^6$ represents hydrogen, methyl, ethyl, C$_3$ alkenyl, C$_3$ alkynyl or cyclopropyl.

10. A method as defined in claim 9 which is in the S enantiomeric isomer form.

11. A method as defined in claim 9 wherein Ar is

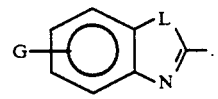

12. A method as defined in claim 9 wherein Ar is

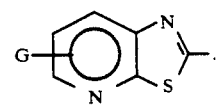

* * * * *